United States Patent
Elliott et al.

(10) Patent No.: US 10,016,509 B1
(45) Date of Patent: *Jul. 10, 2018

(54) NUTRITIONAL SUPPLEMENT COMPOSITIONS CONTAINING C60-FULLERENE-PHYTONUTRIENT-TRIGLYCERIDE COMPLEXES FOR SUB-CELLULAR PHYTONUTRIENT DELIVERY

(71) Applicant: NextGen Research, Greenville, SC (US)

(72) Inventors: Bevan Craig Elliott, Greenville, SC (US); Jonathan David Griffith, Greenville, SC (US)

(73) Assignee: NextGen Research, Greenville, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/180,825

(22) Filed: Jun. 13, 2016

Related U.S. Application Data

(63) Continuation-in-part of application No. 14/507,125, filed on Oct. 6, 2014, now Pat. No. 9,682,150.

(60) Provisional application No. 62/174,587, filed on Jun. 12, 2015, provisional application No. 61/886,769, filed on Oct. 4, 2013, provisional application No. 61/886,770, filed on Oct. 4, 2013.

(51) Int. Cl.

| | |
|---|---|
| *A61K 31/05* | (2006.01) |
| *A61K 31/122* | (2006.01) |
| *A61K 31/409* | (2006.01) |
| *A23L 33/12* | (2016.01) |
| *A23L 33/165* | (2016.01) |
| *A61K 47/48* | (2006.01) |

(52) U.S. Cl.
CPC ........ *A61K 47/48015* (2013.01); *A23L 33/12* (2016.08); *A23L 33/165* (2016.08); *A61K 31/05* (2013.01); *A61K 31/122* (2013.01); *A61K 31/409* (2013.01); *A23V 2002/00* (2013.01)

(58) Field of Classification Search
CPC .. A61K 2300/00; A61K 35/618; A61K 36/63; A61K 38/05; A61K 38/07; A61K 38/4886; A61K 31/05; A61K 31/122; A61K 31/202; A61K 31/409; A61K 31/355; A61K 31/00; A61K 31/015; A61K 38/4806; A61K 47/44; A61K 47/04; A61K 47/48015; A23K 1/16; A23K 1/164; A23K 1/1646; A23K 1/1653; A23K 1/1806

See application file for complete search history.

(56) References Cited

U.S. PATENT DOCUMENTS

| | | | |
|---|---|---|---|
| 8,058,483 B2 * | 11/2011 | Koruga | A61K 8/19 424/489 |
| 9,682,150 B1 * | 6/2017 | Gitterle | A61K 47/48015 |
| 2008/0260849 A1 | 10/2008 | Aimi et al. | |
| 2010/0150853 A1 | 6/2010 | Cassin et al. | |
| 2011/0250178 A1 | 10/2011 | Brooks et al. | |

OTHER PUBLICATIONS

Ikeda, J. Incl. Phenom Macrocycl Chem (2013) 77: 49-65, "Water-soluble fullerenes using sol. agents, and their appl . . . ", published Apr. 24, 2013.*

* cited by examiner

*Primary Examiner* — Debbie K Ware
(74) *Attorney, Agent, or Firm* — Dinsmore & Shohl, LLP

(57) ABSTRACT

Nutritional supplement compositions that may provide sub-cellular phytonutrient delivery include a carrier oil base containing at least one triglyceride and also contain at least one biologically active complex in the carrier oil base. The biologically active complex may include a non-covalent complex of a carbon-60 fullerene, phytonutrient compound, and a triglyceride from the carrier oil base. The phytonutrient compound may be chosen from compounds having the ability to form non-covalent complexes with six-membered aromatic rings of carbon-60 fullerene. Examples of such phytonutrient compound include, for example, phenolic compounds, polyphenolic compounds, phenolic acids, flavonoids, terpenoids, tannins, stilbenes, curcuminoids, coumarins, lignans, quinones, phenylethanoids, carotenoids, astaxanthin, zeaxanthin, or coenzyme Q10. The nutritional supplement compositions may include multiple biologically active complexes in which the phytonutrient compounds are derived from olives, algae, or both. The nutritional supplement compositions may mitigate various diseases or disorders for which inflammation is an etiologic factor.

20 Claims, No Drawings

NUTRITIONAL SUPPLEMENT COMPOSITIONS CONTAINING C60-FULLERENE-PHYTONUTRIENT-TRIGLYCERIDE COMPLEXES FOR SUB-CELLULAR PHYTONUTRIENT DELIVERY

CROSS-REFERENCES TO RELATED APPLICATIONS

This application claims the benefit of priority under 35 U.S.C. § 119(e) to U.S. Provisional Application Ser. No. 62/174,587, filed Jun. 12, 2015, and is also a continuation-in-part of U.S. application Ser. No. 14/507,125, filed Oct. 6, 2014, which claims the benefit of priority to U.S. Provisional Application Ser. No. 61/886,769, filed Oct. 4, 2013, and to U.S. Provisional Application Ser. No. 61/886,770, filed Oct. 4, 2013. All of the foregoing documents are incorporated by reference herein in their entirety.

TECHNICAL FIELD

The present application relates generally to dietary supplements and, more particularly, to dietary supplements containing a fullerene complex that may decrease multi-system symptoms of inflammation and aging in vivo.

BACKGROUND

The "old paradigm" of disease management reflects a tendency to view the maladies affecting humans and other animals as a multitude of diseases. Many diseases require a multitude of approaches, because they fail to address the common underlying mechanism among virtually all disease processes: inflammation. An emerging paradigm seeks to tie inflammation-related disease processes together, and treat them at their root cause; i.e. inflammation, rather than downstream, via a host of less effective treatments which fail to address the root cause.

Regardless of etiology, most diseases eventually produce significant inflammation at the cell, tissue, organ, or systemic level, making inflammation a key therapeutic target in the majority of diseases, regardless of etiology.

As more and more diseases begin to fall under the umbrella of inflammation, it becomes clear that an opportunity exists to simplify management of disease, improve quality of life, and reduce the cost of care. This opportunity resides in the provision of an effective, broad-based, adjunctive or "complementary" treatment modality which addresses inflammation in all tissues.

There are on-going needs for dietary supplements having antioxidant properties and the ability to combat the effects of inflammation.

SUMMARY

Against the above background, embodiments of this specification are directed to nutritional supplement compositions. The nutritional supplement compositions may include sub-cellular phytonutrient delivery supplements that have nutritional benefits for humans. The nutritional supplement compositions may include a carrier oil base containing at least one triglyceride. The nutritional supplement compositions may further include at least one biologically active complex in the carrier oil base. The at least one biologically active complex may have a first portion and a second portion. The first portion may include comprising a carbon-60 fullerene non-covalently associated with a phytonutrient compound. The second portion may include a triglyceride from the carrier oil base non-covalently associated with the first portion. According to some embodiments, the nutritional supplement compositions optionally may contain one or more additional ingredients dissolved in or reacted in the carrier oil base. The one or more additional ingredients may include, for example, uncomplexed carbon-60 fullerene, uncomplexed oleocanthal, uncomplexed oleacein, uncomplexed oleuropein, uncomplexed hydroxytyrosol, uncomplexed astaxanthin, or uncomplexed coenzyme $Q_{10}$. The supplements may have antioxidant or anti-inflammatory properties and also may function as a cellular mitochondrial and electron-transport chain revitalizer. The supplements may improve an organism's response to toxins, may decrease risks of various infarctions, may mitigate mitochondrial dysfunction, may decrease multi-system symptoms of inflammation in vivo, or combinations of these.

According to further embodiments, nutritional supplement compositions may include a carrier oil base containing at least one triglyceride. The nutritional supplement compositions may further include at least one biologically active complex in the carrier oil base. The at least one biologically active complex may have a first portion and a second portion. The first portion may include comprising a carbon-60 fullerene non-covalently associated with a phytonutrient compound. The second portion may include a triglyceride from the carrier oil base non-covalently associated with the first portion. The carrier oil base may be chosen from olive oils, argan oils, medium-chain triglyceride oils, and combinations thereof. The at least one biologically active phenolic compound may include oleocanthal, oleacein, oleuropein, tyrosol, hydroxytyrosol, astaxanthin, zeaxanthin, coenzyme Q10, or combinations thereof.

Additional features and advantages of the embodiments described herein will be set forth in the detailed description that follows. Such additional features and advantages should be readily apparent to those skilled in the art or recognized by practicing the embodiments described in the detailed description and the claims following the detailed description. It should be understood that both the foregoing general description and the following detailed description describe various embodiments and are intended to provide an overview or framework for understanding the nature and character of the claimed subject matter.

DETAILED DESCRIPTION

References will now be made in detail to various embodiments of nutritional supplement compositions. It should be understood that the descriptions of particular embodiments are not intended to be limiting, particularly with respect to routine variations within the grasp of the person having ordinary skill.

As used herein, the term "non-covalently associated with" with regard to two or more molecules means that the two or more molecules behave in a solution as a single entity, even in the absence of a covalent bond between or among the two or more molecules. Examples of non-covalent associations include physical and chemical associations such as van der Waals interactions.

As used herein, the term "complex" includes all aspects of chemical complexes understood according to the plain and ordinary meaning of the term "complex" to those skilled in the art. It should be understood, therefore, that the term "complex" implies that two or more chemical entities or compounds behave as a single entity in a solution, even in the absence of a covalent bond between or among the two or more chemical entities or compounds.

As used herein, the term "uncomplexed" with respect to any ingredient of a nutritional supplement composition other than carbon-60 fullerene means that the ingredient is not a part or a portion of a complex including a carbon-60 fullerene. Thus, an "uncomplexed" ingredient according to this definition may nevertheless be a part or a portion of a chemical complex, provided it is not a part or a portion of a complex including a carbon-60 fullerene. The term "uncomplexed carbon-60 fullerene" means carbon-60 fullerene that is neither covalently bonded nor non-covalently associated with any other molecule.

A nutritional supplement composition according to embodiments may include a carrier oil base containing at least one triglyceride. The nutritional supplement compositions may further include at least one biologically active complex in the carrier oil base. In some embodiments, the biologically active complex includes a first portion and a second portion. The first portion may include a carbon-60 fullerene non-covalently associated with a phytonutrient compound. The second portion may include a triglyceride, such as a triglyceride from the carrier oil base, non-covalently associated with the first portion. In some embodiments, the at least one biologically active complex may be a non-covalent complex of carbon-60 fullerene, a phytonutrient compound, and a triglyceride. In some embodiments, the nutritional supplement composition may be an oil-based nutritional supplement for humans. The nutritional supplement compositions may be suitable for administration orally or by any other suitable method to a subject in need thereof, such as a human subject, for example. The subject in need of the nutritional supplement composition may exhibit one or more forms of bodily inflammation.

The nutritional supplement compositions include a carrier oil base. The carrier oil base may contain at least one triglyceride. In some embodiments, the carrier oil base may be a triglyceride oil containing medium-chain triglycerides. Medium-chain triglycerides include triglycerides formed from three molecules of fatty acid and one molecule of glycerol, in which at least two of the three molecules of fatty acid are medium-chain fatty acids having an aliphatic tail of 6 to 12 carbon atoms. Medium-chain fatty acids include, for example, caproic acid ($C_6$), caprylic acid ($C_8$), capric acid ($C_{10}$), and lauric acid ($C_{12}$). In other embodiments, the carrier oil base may be any pharmaceutically acceptable oil, to which one or more triglycerides have been added.

In some embodiments, the carrier oil base may be or may include olive oil, argan oil, combinations thereof, or isolated components thereof, including but not limited to olive-oil derived triglycerides, argan-oil derived triglycerides, or combinations of these. The at least one triglyceride of the carrier oil base may be a triglyceride formed from fatty acids that have either saturated or unsaturated aliphatic carbon chains. In some embodiments, the at least one triglyceride of the carrier oil base may be a triglyceride formed from at least one unsaturated aliphatic carbon chain, that is, at least one aliphatic carbon chain that includes at least one double bond.

Triglycerides in olive oils generally include those formed from fatty acids such as oleic acid, linoleic acid, palmitic acid, stearic acid, and α-linolenic acid. Triglycerides in argan oil generally include those formed from fatty acids such as oleic acid, linoleic acid, palmitic acid, stearic acid, and linolenic acid. It should be understood that olive oil and argan oil may contain triglycerides from other fatty acids. In an illustrative embodiment, the at least one triglyceride present in the carrier oil base of the nutritional supplement compositions may include, for example, triolein, which is formed from three molecules of oleic acid and one molecule of glycerol. Many olive oils include approximately 4% to 30% by weight triolein, based on the total weight of the olive oil. The at least one triglyceride present in the carrier oil base may include, for example, any triglyceride formed from three molecules of any fatty acid present in olive oil or argan oil and one molecule of glycerol. Such triglycerides may be formed from three molecules of one fatty acid, from two molecules of a first fatty acid and one molecule of a second fatty acid different from the first fatty acid, or from one molecule each of three different fatty acids.

The nutritional supplement compositions further include at least one biologically active complex in the carrier oil base. The at least one biologically active complex may be or may include a non-covalent complex of a biologically active compound with a carbon-60 fullerene and a triglyceride of the carrier oil base. Thus, the nutritional supplement compositions contain one or more than one biologically active complex, each of which has three components: a molecule of carbon-60 fullerene, a molecule of a biologically active compound, and a molecule of a triglyceride from the carrier oil. In some embodiments, the biologically active compounds may be a phytonutrient compound.

The biologically active complex or complexes of the nutritional supplement compositions include a molecule of carbon-60 fullerene. Carbon-60 fullerene, also known as $C_{60}$, buckminsterfullerene, or bucky-ball carbon, is a spherical fullerene molecule that includes twenty hexagonal six-carbon aromatic rings and twelve pentagonal five-carbon rings fused to form a spherical structure with a carbon atom at each vertex of a hexagon or pentagon and a bond along each edge of the hexagons and pentagons. Uncomplexed carbon-60 fullerene is soluble in pharmaceutically acceptable carrier oils containing triglycerides. Carbon-60 fullerene is known to have an affinity to mitochondrial membranes within animal cells and is also known to be a powerful catalytic antioxidant. However, uncomplexed carbon-60 fullerene is generally not capable of passing through the cellular phospholipid membrane or the blood/brain barrier, a general prerequisite of having therapeutic efficacy with regard to the mitochondrial membranes. The carbon-60 fullerene of the nutritional supplement compositions according to embodiments may be derived from any source, including from natural sources such as soot, carbon black, molasses, shungite, shilajit, and meteoritic solids, or from synthetic laboratory manufacture by any known technique.

The biologically active complex or complexes of the nutritional supplement compositions include a molecule of a biologically active compound. The biologically active compound may be a compound having a chemical structure that enables the biologically active compound to associate itself with a molecule of carbon-60 fullerene by a non-covalent chemical interaction or attractive force. In some embodiments, the biologically active compound may be a phytonutrient compound. Phytonutrient compounds include compounds such as phenolic compounds, polyphenolic compounds, phenolic acids, flavonoids, terpenoids, tannins, stilbenes, curcuminoids, coumarins, lignans, quinones, phenylethanoids, carotenoids, astaxanthin, zeaxanthin, coenzyme Q10, or derivatives of any of these, which occur naturally in plants or are synthetically prepared to mimic the structure or properties of equivalent compounds found in plants. In some embodiments, the biologically active compound may be a phytonutrient made from natural, organic, or non-genetically-modified sustainable plant sources.

Phytonutrient compounds may have known biological significance, including nutritional value, but may not be essential nutrients to animals or humans. Specific examples of phytonutrient compounds include, but are not limited to phenols or polyphenols such as oleocanthal from olive leaf, olive fruit, and/or olive oil; oleacein from olive leaf, olive fruit, and/or olive oil; oleuropein from olive leaf, olive fruit, and/or olive oil; hydroxytyrosol from olive leaf, olive fruit, and/or olive oil; astaxanthin from microalgae; zeaxanthin from green leafy or yellow vegetables; carvacrol from oregano, pepperwort, or wild bergamot; and honokiol from bark, seed cones, or leaves of trees belonging to the genus *Magnolia*. Oleocanthal is a phenolic compound that has been shown to act as a broad-based, potent anti-inflammatory or anti-cancer agent. Oleacein is a phenolic compound that has been shown to act as a potent anti-inflammatory and anti-oxidant. Oleuropein is a phenolic compound that has been shown to act as a potent anti-inflammatory, anti-oxidant, antimicrobial, anti-cancer, and anti-viral agent. Hydroxytyrosol is a phenolic compound that has been shown to act as a potent anti-inflammatory and anti-oxidant. Honokiol is a phenolic compound that has been shown to act as an anti-inflammatory, an antioxidant, and an anti-cancer agent. In certain embodiments, astaxanthin from microalgae may include fatty acid esters of astaxanthin. Astaxanthin itself is one of the most powerful anti-oxidants discovered to date, with brain protective and eye health effects noted in the literature, because it can cross the blood-ocular barrier and the blood-brain barrier. Astaxanthin fatty acid esters may be solubilized in triglycerides.

In illustrative embodiments, the biologically active compound, such as a phytonutrient compound, may be a compound having a chemical structure that enables the biologically active compound to associate itself non-covalently such as by van der Waals attraction, to a molecule of carbon-60 fullerene. Such a van der Waals attraction may result from hybrid π-π, or polar-π interactions of an aromatic ring of the carbon-60 fullerene molecule and one or more double bonds present in the biologically active compound. In some embodiments, the biologically active compound may have a six-carbon ring with at least one double bond or an aromatic six-carbon ring with three double bonds, for example. In such embodiments, the biologically active complex may include a non-covalent chemical attraction between the at least one double bond of the six-carbon ring of the biologically active compound and a six-membered aromatic ring of the carbon-60 fullerene.

The biologically active complex or complexes of the nutritional supplement compositions may include a first portion that is or includes a carbon-60 fullerene non-covalently associated with the biologically active compound or phytonutrient compound. In some embodiments, the first portion of the biologically active complexes may be complexes of carbon-60 and phenolic phytonutrient compounds that may be represented by a general structure (I) or (II):

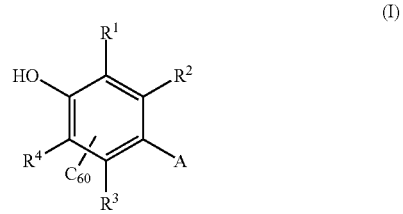

(I)

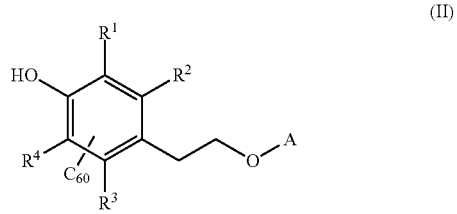

(II)

In the general structures (I) and (II), group A is an alkyl moiety, and groups $R^1$, $R^2$, $R^3$, and $R^4$ are independently hydrogen, hydroxyl, or alkyl. In other embodiments including but not limited to those in which the first portion has a structure according to general structure (I) or (II), the first portion of the biologically active complexes may include non-covalent complexes of carbon-60 and any of the phytonutrient compounds of Table 1. In such biologically active complexes, an aromatic six-carbon ring of the carbon-60 fullerene is non-covalently associated with a double bond of the phytonutrient compound such as, for example, a double bond in an aromatic ring of the phytonutrient compound or a double bond of a non-aromatic six-carbon ring of the phytonutrient compound.

TABLE 1

Examples of phytonutrient compounds

| Compound | Structure |
|---|---|
| Oleocanthal | 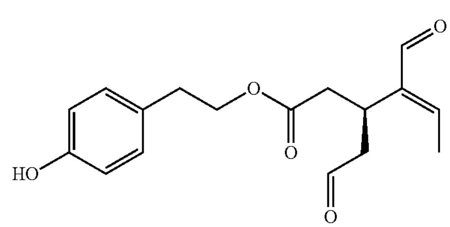 [SMILES: C/C=C(/C=O)[C@@H](CC=O)CC(=O)OCCc1ccc(O)cc1] |

TABLE 1-continued

Examples of phytonutrient compounds

| Compound | Structure |
|---|---|
| Oleacein | 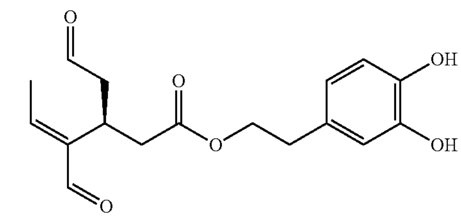 [SMILES: C/C=C(/C=O)[C@@H](CC=O)CC(=O)OCCc1ccc(O)c(O)c1] |
| Oleuropein | 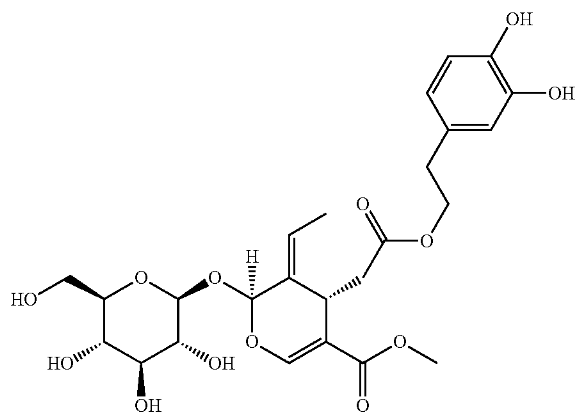 [SMILES: C/C=C1/[C@H](O[C@@H]2O[C@H](CO)[C@@H](O)[C@H](O)[C@H]2O)OC=C(C(=O)OC)[C@H]1CC(=O)OCCc1ccc(O)c(O)c1] |
| Tyrosol | 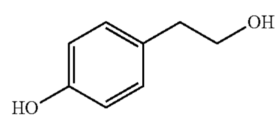 |
| Hydroxytyrosol | 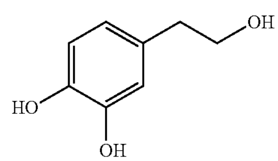 [SMILES: OCCc1ccc(O)c(O)c1] |
| Astaxanthin | 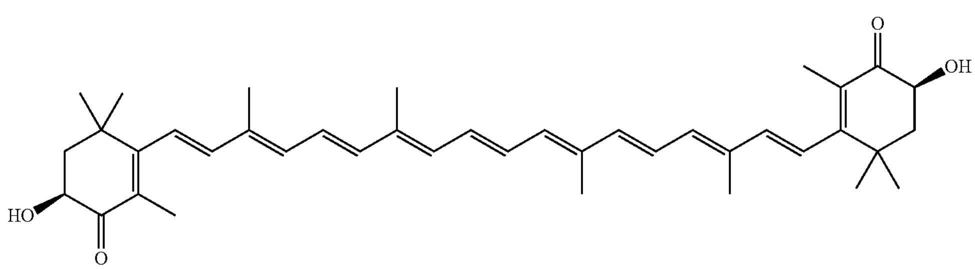 [SMILES: CC1=C(/C=C/C(C)=C/C=C/C(C)=C/C=C/C=C(C)/C=C/C=C(C)/C=C/C2=C(C)C(=O)[C@@H](O)CC2(C)C)C(C)(C)C[C@H](O)C1=O] |
| Zeaxanthin | 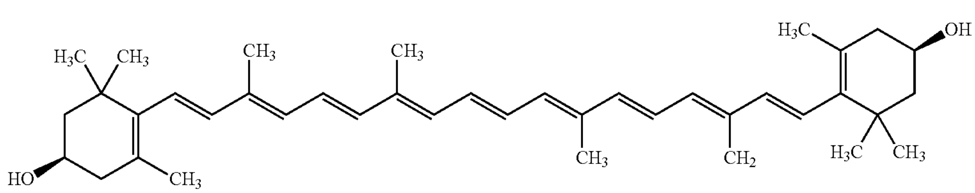 [SMILES: CC1=C(/C=C/C(C)=C/C=C/C(C)=C/C=C/C=C(C)/C=C/C=C(C)/C=C/C2=C(C)C[C@@H](O)CC2(C)C)C(C)(C)C[C@H](O)C1] |

TABLE 1-continued

Examples of phytonutrient compounds

| Compound | Structure |
| --- | --- |
| Coenzyme Q10 | (structure) |
| Carvacrol | (structure) |
| Honokiol | (structure) |

The biologically active complex or complexes of the nutritional supplement compositions may include a second portion that is or includes a molecule of a triglyceride from the carrier oil base non-covalently associated with the first portion, that is, with the carbon-60 fullerene non-covalently associated with the biologically active compound or phytonutrient compound. Accordingly to embodiments, triglycerides of the base carrier oil may include triglycerides that are a primary component of the base carrier oil or triglycerides that are dissolved in or solvated in the base carrier oil. Examples of triglycerides that may be present in the base carrier oil have been discussed previously.

In general, triglycerides include aliphatic carbon chains that extend as three arms from a glycerol-derived moiety. Without intent to be bound by theory, in the nutritional supplement compositions according to embodiments, it is believed that the aliphatic carbon chains of the triglycerides in the carrier oil base may wrap themselves around, encage, or otherwise non-covalently interact with the biologically active compound and the molecule of carbon-60 fullerene non-covalently bound to the biologically active compound.

In this regard, triglyceride molecules non-covalently associated with the biologically active complex as one of the three components of the biologically active complex are distinguishable from other molecules of the triglyceride that may be present in the carrier oil base. That is, the carrier oil base of nutritional supplement compositions may include both free (uncomplexed) triglycerides and complexed triglycerides that are a component of a biologically active complex. In particular, it is believed that, the triglyceride molecules associated with the biologically active complex may not only increase the solubility of the other two components of the biologically active complex but also may enable the other two components of biologically active complex to penetrate cellular phospholipid membranes, for example. In vivo, the triglyceride may be metabolized into glycerin and fatty acids, and at least one of the fatty acids will remain associated with the biologically active complex including the carbon-60 fullerene and the biologically active compound or phytonutrient compound. It is believed that the retention of the fatty acid may facilitate penetration of the biologically active complex through the cellular phospholipid membrane and/or the blood brain barrier.

In some embodiments, the triglycerides from the base carrier oil may include fatty acids having a low level of chemical reactivity with carbon-60 fullerene, particularly fatty acids that are not highly susceptible to cycloadditions or radical reactions with carbon-60 fullerene. For a fatty acid to undergo a cycloaddition reaction with a carbon-60 fullerene, at least two double bonds on adjacent carbons are required. Small amounts of linoleic acid and linolenic acid in olive oils have been found to react in this manner if the double bonds of these acids are subjected to conditions by which they can rearrange. On the other hand, olive-oil triglycerides contain a large about of oleic acid, which has only one double bond. Though mono-unsaturated fatty acids such as oleic acid can undergo radical addition to carbon-60 fullerene, intense conditions involving ultraviolet irradiation and oxygen are required. Therefore, in some embodiments the second portion of the biologically active complex of the nutritional supplement compositions may include triglycerides of which one, two, or all three of the fatty acids is/are a monounsaturated fatty acid.

The triglycerides from the base carrier oil may also include specific triglycerides known to have an ability to penetrate certain cell membranes. A non-limiting example of a triglyceride known to have an ability to penetrate certain cell membranes is triolein, a triglyceride prevalent in olive oils, which is known to have an ability to penetrate phospholipid membranes, for example. Triolein is also a triglyceride of which all three of the fatty acids are a monounsaturated fatty acid, particularly, oleic acid. In general, the ability of the triglyceride from the carrier oil base to facilitate penetration of the biologically active complex may vary with respect to fatty-acid chain lengths and degrees of unsaturation of the fatty acids that make up the triglyceride. For example, both short-chain saturated fatty acids (aliphatic tail of fewer than six carbon atoms) and medium-chain saturated fatty acids (aliphatic tail of six to twelve carbon atoms) can penetrate the blood-brain barrier. It is also generally accepted that fatty-acid transport proteins (FATP) in the cell membrane lipid bilayer control the extent and kinetics of penetration of a fatty acid through a cell membrane.

In some embodiments, the nutritional supplement compositions include one biologically active complex in the carrier oil base. In other embodiments, the nutritional supplement compositions further include a plurality of biologically active complexes in the carrier oil base. In such embodiments, the plurality of biologically active complexes may include multiple non-identical biologically active complexes, differing from each other with respect to the first portion of the biologically active complex (that is, the biologically active compound or phytonutrient compound non-covalently associated with the carbon-60 fullerene), to the second portion of the biologically active complex (that is, the particular triglyceride of the carrier oil base non-covalently associated with the first portion of the biologically active complex), or to both the first portion and the second portion of the biologically active complex.

In illustrative embodiments, the nutritional supplement compositions may include at least one biologically active complex chosen from non-covalent carbon-60 fullerene-oleocanthal-triglyceride complexes; non-covalent carbon-60 fullerene-oleacein-triglyceride complexes; non-covalent carbon-60 fullerene-oleuropein-triglyceride complexes; non-covalent carbon-60 fullerene-tyrosol-triglyceride complexes; non-covalent carbon-60 fullerene-hydroxytyrosol-triglyceride complexes; non-covalent carbon-60 fullerene-carvacrol-triglyceride complexes; non-covalent carbon-60 fullerene-honokiol-triglyceride complexes; non-covalent carbon-60 fullerene-astaxanthin-triglyceride complexes; non-covalent carbon-60 fullerene-zeaxanthin-triglyceride complexes; non-covalent carbon-60 fullerene-coenzyme-Q10-triglyceride complexes in which coenzyme Q10 is in the form of ubiquinone, semiquinone, or ubiquinol; or combinations thereof.

In illustrative embodiments, the nutritional supplement compositions may include at least one biologically active complex chosen from non-covalent carbon-60 fullerene-oleocanthal-triolein complexes; non-covalent carbon-60 fullerene-oleacein-triolein complexes; non-covalent carbon-60 fullerene-oleuropein-triolein complexes; non-covalent carbon-60 fullerene-hydroxytyrosol-triolein complexes; non-covalent carbon-60 fullerene-coenzyme-Q10-triolein complexes in which coenzyme Q10 is in the form of ubiquinone, semiquinone, or ubiquinol; or combinations thereof.

In some embodiments, the nutritional supplement compositions may include (1) at least one biologically active complex in which the biologically active compound thereof is a phytonutrient compound derived from olives and (2) at least one biologically active complex in which the biologically active compound thereof is a phytonutrient compound derived from algae or vegetables. In such embodiments, the at least one biologically active complex in which the phytonutrient compound is derived from olives may be chosen from non-covalent carbon-60 fullerene-oleocanthal-triglyceride complexes, non-covalent carbon-60 fullerene-oleacein-triglyceride complexes, non-covalent carbon-60 fullerene-oleuropein-triglyceride complexes, non-covalent carbon-60 fullerene-tyrosol-triglyceride complexes, non-covalent carbon-60 fullerene-hydroxytyrosol-triglyceride complexes, or combinations thereof. The at least one biologically active complex in which the phytonutrient compound is derived from algae or vegetables may be chosen from non-covalent carbon-60 fullerene-astaxanthin-triglyceride complexes, non-covalent carbon-60 fullerene-zeaxanthin-triglyceride complexes, or combinations thereof. In some embodiments, the triglyceride portion of such biologically active complexes may include triolein. In some embodiments, such nutritional supplement compositions may additionally include at least one of an uncomplexed coenzyme Q10 or a non-covalent carbon-60 fullerene-coenzyme-Q10-triglyceride complex.

The biologically active complexes of the nutritional supplement compositions may be prepared by any suitable synthetic procedure. The biologically active complexes may be isolated and subsequently added to the nutritional supplement compositions or may be prepared by processing the nutritional supplement compositions in a manner that forms the biologically active complexes. The biologically active complexes do not form in significant or efficacious amounts within a mixture of a triglyceride-containing oil, carbon-60 fullerene, and a biologically active compound or phytonutrient compound that is not intentionally subjected to further processing steps to form the biologically active complexes. Exemplary processing steps that may form the biologically active complexes will now be described in greater detail in the Examples section of this disclosure.

The nutritional supplement compositions according to embodiments may further include one or more optional ingredients that may impart additional nutritional benefits. The one or more optional ingredients may be dissolved or solvated in the carrier oil base in combination with the at least one biologically active complex. In some embodiments, the one or more optional ingredients may be uncomplexed ingredients not non-covalently associated with a molecule of carbon-60 fullerene. For example, the nutritional supplement compositions may further include uncomplexed phenols or uncomplexed polyphenols; uncomplexed oleocanthal; uncomplexed oleacein; uncomplexed oleuropein; uncomplexed hydroxytyrosol; uncomplexed astaxanthin; uncomplexed zeaxanthin; uncomplexed tyrosol; uncomplexed carvacrol; uncomplexed honokiol; uncomplexed coenzyme $Q_{10}$ as ubiquinone, semiquinone, or combinations thereof; or any combination of these. The one or more optional ingredients may include uncomplexed carbon-60 fullerene.

In illustrative embodiments, the nutritional supplement compositions may include at least one additional ingredient dissolved in the carrier oil base and chosen from an uncomplexed carbon-60 fullerene; an uncomplexed biologically active phenol; an uncomplexed biologically active polyphenol; uncomplexed astaxanthin; uncomplexed zeaxanthin; or uncomplexed coenzyme Q10 in the form of ubiquinone, semiquinone, ubiquinol, or a combination thereof. In further illustrative embodiments, the nutritional supplement compositions may include all of the following additional ingredients dissolved in the carrier oil base: uncomplexed carbon-60 fullerene; at least one uncomplexed biologically active phenolic compound or polyphenol; uncomplexed astaxanthin; uncomplexed zeaxanthin; and uncomplexed coenzyme Q10 in the form of ubiquinone, semiquinone, ubiquinol, or a combination thereof.

In further illustrative embodiments, the nutritional supplement compositions may include at least one biologically active complex and at least one of uncomplexed astaxanthin, uncomplexed zeaxanthin, and/or uncomplexed coenzyme Q10. In such embodiments, the at least one biologically active complex may include any biologically active complex described in this specification or may include, for example, non-covalent carbon-60 fullerene-oleocanthal-triglyceride complexes, non-covalent carbon-60 fullerene-oleacein-triglyceride complexes, non-covalent carbon-60 fullerene-oleuropein-triglyceride complexes, or combinations thereof. In some embodiments, the triglyceride portion of such biologically active complexes may include triolein.

The nutritional supplement compositions according to some embodiments may be oil-based nutritional supplements that may be administered to a subject in need thereof, such as an animal subject or a human subject in need thereof. The subject in need may exhibit one or more forms of bodily inflammation. Administration may be by oral administration.

In some embodiments, the nutritional supplement compositions be formulated as an oil-based nutritional supplement for animals or humans that contains ingredients in the following concentrations, based on a mass of an ingredient per unit volume of the nutritional supplement composition: a carbon-60 fullerene concentration of from 0.1 g/L to 3 g/L; a phenolic concentration of from 100 µg/L (ppm) to 4,000 µg/L; an astaxanthin concentrations of from 0.1 g/L to 10 g/L grams per liter; and a coenzyme $Q_{10}$ concentrations of from 0.1 g/L to and 3 g/L.

The carbon-60 fullerene concentration of the nutritional supplement composition is based on a total amount of (a) complexed carbon-60 fullerene from all biologically active complexes in the nutritional supplement composition and (b) any uncomplexed carbon-60 fullerene present in the nutritional supplement composition, per unit volume of the nutritional supplement composition. The phenolic concentration of the nutritional supplement composition is based on a total amount of (a) complexed phenolic compounds from all biologically active complexes in the nutritional supplement composition and (b) any uncomplexed phenolic compound present in the nutritional supplement composition, per unit volume of the nutritional supplement composition. The astaxanthin concentration of the nutritional supplement composition is based on a total amount of (a) complexed astaxanthin from all biologically active complexes in the nutritional supplement composition and (b) any uncomplexed astaxanthin present in the nutritional supplement composition, per unit volume of the nutritional supplement composition. The coenzyme Q10 concentration of the nutritional supplement composition is based on a total amount of (a) complexed coenzyme Q10 in any form from all biologically active complexes in the nutritional supplement composition and (b) any uncomplexed coenzyme Q10 in any form present in the nutritional supplement composition, per unit volume of the nutritional supplement composition.

The nutritional supplement compositions may be formulated by dissolving all ingredients into the base carrier oil and reacting the ingredients to form the biologically active complexes, or by first forming the biologically active complexes in the base carrier oil and subsequently dissolving additional ingredients into the base carrier oil containing the one or more biologically active complexes. Mixing and dissolving of the various ingredients may be carried out under any suitable temperature and pressure conditions. After administration to a subject in need thereof, the nutritional supplement compositions may penetrate the phospholipid bilayer of cells of the subject and may deliver both carbon-60 fullerene and the biologically active compound or phytonutrient compound of the biologically active complex into the cell endoplasmic reticula, nuclear membranes, mitochondrial membranes, or mitochondria of the cells of the subject. Thereby, the nutritional supplement compositions may facilitate the bioavailability of antioxidant compounds such as carbon-60 fullerene and phytonutrient compounds to the cells of the subject, so as to provide anti-oxidant, anti-inflammatory, anti-cancer, and other beneficial biological processes in vivo.

In some embodiments, the nutritional supplement compositions may deliver carbon-60 fullerene and phytonutrient compounds sub-cellularly into various cell types to mitigate inflammation symptoms via mechanisms including COX-1 and COX-2 inhibition. In some embodiments, one or more biologically active complexes in the nutritional supplement compositions according to embodiments previously described may be delivered sub-cellularly across the blood-brain barrier into various cell types to mitigate dementia, Parkinson's disease, or Alzheimer's disease. In some embodiments, one or more biologically active complexes in the nutritional supplement compositions according to embodiments previously described may be delivered sub-cellularly into various cell types to induce apoptosis in various cancer cells in vivo or to induce cell death via lysosomal membrane permeabilization.

In illustrative embodiments, a nutritional supplement composition containing a biologically active complex of carbon-60, oleacin, and triolein may be delivered sub-cellularly into various cell types to cause mitigation of risk of myocardial and cerebral infarction via inhibition of myeloperoxidase and metalloproteinase-9 production, inhibition of activation of Nrf2/heme oxygenase-1 pathway, and enabling the complexation of oleacein with hemoglobin and haptoglobin. In some embodiments, the biologically active complex of carbon-60, oleacin, and triolein may be delivered sub-cellularly into various cell types to cause mitigation of allergy and asthma symptoms via inhibition of 5-lipoxygenase.

In some embodiments, nutritional supplement compositions containing a biologically active complex of carbon-60, a phytonutrient compound, and triolein, in which the phytonutrient compound is oleocanthal, oleacein, oleuropein, or hydroxytyrosol, or combinations thereof, may be delivered sub-cellularly into the mitochondrial membranes of the subject to mitigate mitochondrial dysfunction.

In some embodiments, nutritional supplement compositions containing a biologically active complex of carbon-60, astaxanthin, and a triglyceride may be delivered into the cellular phospholipid bilayer to form a molecular bridge across the bilayer and effectively inhibit oxidation of the phospholipids.

In some embodiments, nutritional supplement compositions containing a biologically active complex of carbon-60, coenzyme $Q_{10}$, and a triglyceride may be delivered sub-cellularly to the mitochondrial membranes, acting as an anti-oxidant, and protecting or restoring the electron transport chain in the membranes.

In some embodiments, nutritional supplement compositions containing a biologically active complex of carbon-60, honokiol, and a triglyceride may be delivered sub-cellularly to the mitochondrial membranes, acting as an anti-inflammatory, an anti-oxidant, and an anti-cancer agent.

Nutritional supplement compositions according to further embodiments may include oleocanthal, oleacein, hydroxytyrosol, oleuropein, astaxanthin, coenzyme $Q_{10}$, extra virgin olive oil, natural colors, and natural flavors. In some embodiments, the nutritional supplement compositions may be free of artificial colors, artificial flavors, or artificial ingredients.

Without intent to be bound by theory, it is believed that through a unique delivery mechanism, the nutritional supplements and complexes contained in the nutritional supplements deliver phytonutrients into cells without loss of effectiveness due to metabolism or poor assimilation. It is believed that the complexes contained in the nutritional supplements are delivered directly into the lipid bilayer, as well as into the nuclear and mitochondrial membranes, which are known to be important in all cellular functions affecting whole body systems. Though many substances, including drugs and nutritional supplements, have been touted to have beneficial effects on the physiology of inflammation and mitochondrial dysfunction, none of them are believed to exhibit comprehensive effects in vivo (in living organisms).

The reason other substances fail to achieve substantive beneficial effects is that they are (1) destroyed during digestion, (2) poorly assimilated through the GI tract, (3) unable to be broadly distributed across various tissues, (4) not distributed on a sub-cellular level, or (5) metabolized or otherwise fail to achieve stable effects inside target sites. In contrast, it is believed that the biologically active complexes contained in the nutritional supplement compositions according to embodiments of this disclosure achieve broad distribution across all tissue types, down to the sub-cellular level. In addition, effects are stable over a reasonably long half-life, so that profound clinical effects may be achieved with either once-daily or twice-daily dosing. It is believed that by delivering active ingredients directly into all cell types and mitochondria, the nutritional supplements described herein may attain broad-based and profound effects at tissue, organ, and organism (whole body) levels.

The effects of the nutritional supplements according to embodiments herein are designed to be ubiquitous in vivo, occurring in all tissue types. This allows the active complexes in the supplements to efficiently address cellular processes that may result in symptoms of inflammation in all tissue types.

In some embodiments, the nutritional supplements described herein may mitigate, reduce, or eliminate many types of inflammation. In turn, the nutritional supplements may have efficacy in mitigating one or more diseases caused directly or indirectly by such inflammation.

Inflammation has been implicated as an etiologic factor in many diseases, affecting one or more organs or organ systems. The nutritional supplement compositions according to embodiments herein may have efficacy for treating one or more inflammation-related diseases or disorders including, but not limited to: heart diseases such as atherosclerosis, cardiomyopathy, myocarditis, and pericarditis; liver diseases such as hepatitis (steatohepatitis), chronic hepatitis due to viral infections, primary sclerosing cholangitis (PSC), and generally suboptimal liver function caused by systemic inflammation; kidney and bladder diseases such as chronic renal insufficiency due to diabetes, glomerulonephritis, inflammatory cystitis, and bladder cancer; lung diseases such as asthma, COPD, emphysema, sarcoidosis, and lung cancer; blood-related or circulatory-related diseases such as vasculitis, leukocytosis, blood cell cancer, and chronic anemia; bone and joint diseases such as osteoarthritis, lupus (SLE), rheumatoid arthritis, and osteoporosis; oral diseases such as periodontitis and Sjögren's syndrome; muscle-related diseases such as inflammatory myopathy, myositis, polymyositis, insulin resistance of muscle cells, and fibromyalgia; brain diseases such as Alzheimer's disease, Parkinson's disease, multiple sclerosis, autism, Asperger's syndrome, amyotrophic lateral sclerosis (ALS), bipolar disorder, and depression; endocrine disorders such as type-II diabetes and Grave's disease; ocular diseases such as macular degeneration, cataracts, uveitis, dry eye, and Sjögren's syndrome; bowel diseases such as Crohn's disease, ulcerative colitis, and irritable bowel syndrome; male sexual diseases such as prostatitis, prostate cancer, and testicular cancer; female sexual diseases such as pelvic inflammatory disease, inflammation of the uterus, inflammation of the fallopian tubes, inflammation of the ovaries, uterine fibroid disease, dysfunctional uterine bleeding, breast cancer, cervical cancer, endometrial cancer, and ovarian cancer; autoimmune diseases; immunodeficiency diseases; cancers, and accelerated cell aging known as "inflamm-aging."

Accordingly, methods for treating inflammation in vivo, may include administering a nutritional supplement composition according to an embodiment of this disclosure to a subject having a disease or disorder involving inflammation. Administration of the nutritional supplement composition may include an oral administration of a liquid composition. The liquid composition may optionally be encapsulated within a suitable capsule such as a gel cap or a soft-gel container that may be swallowed. The subject having the disease or disorder involving inflammation may be administered an effective dose of the one or more active ingredients of the nutritional supplement composition. For example, the subject may be administered a liquid dose of the nutritional supplement composition of from about 0.5 mL to about 30 mL when the nutritional supplement composition includes a carbon-60 fullerene concentration of from 0.1 g/L to 3 g/L; a phenolic concentration of from 100 µg/L (ppm) to 4,000 µg/L; an astaxanthin concentrations of from 0.1 g/L to 10 g/L grams per liter; and a coenzyme $Q_{10}$ concentrations of from 0.1 g/L to and 3 g/L.

Example 1

Formation of a Biologically Active Complex

A biologically active complex of a nutritional supplement composition according to embodiments of this disclosure is prepared by adding an excess of carbon-60 fullerene to a triglyceride oil such as fresh extra virgin (un-oxidized) olive oil or a medium-chain triglyceride oil, up to a carbon-60 fullerene concentration of 3 g/L. An excess of carbon-60 fullerene is reached when no additional carbon-60 fullerene will dissolve in the oil. The oil-fullerene mixture is continuously stirred in a glass, stainless steel, or HDPE vessel and is maintained at from 20° C. to 75° C., in an oxygen partial pressure less than 100 Torr, with all sources of visible, UV, and IR light excluded.

The oil-fullerene mixture is stirred for less than 24 hours, and then a phytonutrient compound such as a phenolic compound, a carotenoid compound, or a ketone is added to the oil-fullerene mixture in at least a 1:1 molar ratio to the total fullerene. If less than a 1:1 ratio of the phytonutrient compound is added, after the reaction, over time, the excess fullerene may react with the fatty acids and corrupt the oil. After addition of the phytonutrient compound, the temperature is reduced to room temperature (24° C.±3° C.).

As the carbon-60 fullerene in the oil complexes with the molecules of the phytonutrient compound, undissolved C60 fullerene still present in the oil before the phytonutrient compound was added begins to dissolve. The reaction proceeds to completion at room temperature over the course of 7 days to 14 days for all carbon-60 fullerene complexes with phytonutrient compound at 1:1 molar ratio, the rate being limited by fatty-acid solubilization. Reaction progress and completion are monitored via UV-Visible absorption bands in the range of 450 nm to 600 nm. Upon reaction completion, if there is no excess un-complexed fullerene, the reaction mixture may be exposed to atmospheric levels of oxygen, but exposure of the complexes to light should be minimized.

Example 2

In Vivo Effectiveness of a Nutritional Supplement Composition

In vivo effectiveness of a nutritional supplement composition according to an embodiment of this disclosure, a non-controlled subjective symptom study was carried out on human volunteer subjects. Twenty subjects anonymously answered weekly subjective symptom questions administered concurrently with a four-week administration of a nutritional supplement composition prepared according to Example 1 and containing a carbon-60 fullerene concentration (including complexed and uncomplexed carbon-60 fullerene) of 0.2 g/L; a phenolic concentration of 0.6 g/L (including complexed and uncomplexed phenolic compounds oleocanthal, oleacein, oleuropein, and hydroxytyrosol); and an astaxanthin concentration of 0.4 g/L in extra-virgin olive oil as the base carrier oil. The nutritional supplement composition of this Example 2 contained non-covalent carbon-60 fullerene-oleocanthal-triglyceride complexes, non-covalent carbon-60 fullerene-oleacein-triglyceride complexes, non-covalent carbon-60 fullerene-oleuropein-triglyceride complexes, and non-covalent carbon-60 fullerene-hydroxytyrosol-triglyceride complexes.

Baseline symptom levels were established for each subject, after which each subject began orally self-administering 12.5 mL of the nutritional supplement composition once daily. Symptomology was reported as levels from one to ten, with one representing the mildest manifestation of the symptom and ten representing the strongest manifestation of the symptom. Thus, mild symptoms were defined as levels 1 through 4, and moderate to severe symptoms were defined as levels 5 through 10. Study questions queried symptom levels for chronic pain, allergies/asthma, and arthritis/joint inflammation, all of which are inflammation-related conditions.

With respect to chronic pain, at week one, 55% of subjects reported mild chronic pain (levels 1-4) and 45% reported moderate to severe chronic pain (levels 5-10). After four weeks, 70% of the subjects reported mild chronic pain (levels 1-4) and 30% reported moderate to severe chronic pain (levels 5-10).

With respect to allergies/asthma, at week one, 70% of subjects reported mild allergies/asthma (levels 1-4) and 30% reported moderate to severe allergies/asthma (levels 5-10). After four weeks, 85% of the subjects reported mild allergies/asthma (levels 1-4) and 15% reported moderate to severe allergies/asthma (levels 5-10).

With respect to arthritis/joint inflammation, at week one, 45% of subjects reported mild arthritis/joint inflammation (levels 1-4) and 55% reported moderate to severe arthritis/ joint inflammation (levels 5-10). After four weeks, 75% of the subjects reported mild arthritis/joint inflammation (levels 1-4) and 25% reported moderate to severe arthritis/joint inflammation (levels 5-10).

Thus, the studies were consistent with decreases of pain levels associated with the inflammation-related chronic pain, allergies/asthma, and arthritis/joint inflammation over the course of the four weeks of administration of a nutritional supplement composition according to an embodiment of this disclosure.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that terms like "preferably," "commonly," and "typically" are not utilized herein to limit the scope of the appended claims or to imply that certain features are critical, essential, or even important to the structure or function of the claimed subject matter. Rather, these terms are merely intended to highlight alternative or additional features that may or may not be utilized in a particular embodiment.

What is claimed is:

1. A nutritional supplement composition that is oil-based, the nutritional supplement composition comprising:
    a carrier oil base containing at least one triglyceride; and
    at least one biologically active complex in the carrier oil base, the at least one biologically active complex comprising:
        a first portion comprising a carbon-60 fullerene non-covalently associated with a phytonutrient compound; and
        a second portion comprising a molecule of the at least one triglyceride from the carrier oil base non-covalently associated with the first portion.

2. The nutritional supplement composition of claim 1, wherein:
    the phytonutrient compound is chosen from phenolic compounds, polyphenolic compounds, phenolic acids, flavonoids, terpenoids, tannins, stilbenes, curcuminoids, coumarins, lignans, quinones, phenylethanoids, carotenoids, astaxanthin, zeaxanthin, or coenzyme Q10;
    the phytonutrient compound comprises a six-carbon ring having at least one double bond; and
    the biologically active complex comprises a non-covalent chemical attraction between the at least one double bond of the six-carbon ring and a six-membered aromatic ring of the carbon-60 fullerene.

3. The nutritional supplement composition of claim 2, wherein the non-covalent chemical attraction is a van der Waals interaction.

4. The nutritional supplement composition of claim 1, wherein the phytonutrient compound is chosen from phenolic compounds or polyphenolic compounds.

5. The nutritional supplement composition of claim 1, wherein the phytonutrient compound is a phenolic compound or a polyphenolic compound and is derived from olive fruit, olive leaf, olive oil, or olive pits.

6. The nutritional supplement composition of claim 1, wherein the phytonutrient compound is chosen from oleocanthal, oleacein, oleuropein, tyrosol, hydroxytyrosol, carvacrol, honokiol, astaxanthin, zeaxanthin, or coenzyme Q10.

7. The nutritional supplement composition of claim 1, wherein the at least one biologically active complex is chosen from:
- non-covalent carbon-60 fullerene-oleocanthal-triglyceride complexes;
- non-covalent carbon-60 fullerene-oleacein-triglyceride complexes;
- non-covalent carbon-60 fullerene-oleuropein-triglyceride complexes;
- non-covalent carbon-60 fullerene-tyrosol-triglyceride complexes;
- non-covalent carbon-60 fullerene-hydroxytyrosol-triglyceride complexes;
- non-covalent carbon-60 fullerene-carvacrol-triglyceride complexes;
- non-covalent carbon-60 fullerene-honokiol-triglyceride complexes;
- non-covalent carbon-60 fullerene-astaxanthin-triglyceride complexes;
- non-covalent carbon-60 fullerene-zeaxanthin-triglyceride complexes;
- non-covalent carbon-60 fullerene-coenzyme-Q10-triglyceride complexes in which
  - coenzyme Q10 is in the form of ubiquinone, semiquinone, or ubiquinol; or combinations thereof.

8. The nutritional supplement composition of claim 1, wherein the carrier oil base is chosen from olive oil, argan oil, medium-chain triglyceride oils, oils containing triolein, and combinations thereof.

9. The nutritional supplement composition of claim 1, further comprising at least one additional ingredient dissolved in the carrier oil base and chosen from:
- an uncomplexed carbon-60 fullerene;
- an uncomplexed biologically active phenol;
- an uncomplexed biologically active polyphenol;
- uncomplexed honokiol;
- uncomplexed astaxanthin;
- uncomplexed zeaxanthin; or
- uncomplexed coenzyme Q10 in the form of ubiquinone, semiquinone, ubiquinol, or a combination thereof.

10. The nutritional supplement composition of claim 1, further comprising additional ingredients dissolved in the carrier oil base, the additional ingredients comprising:
- uncomplexed carbon-60 fullerene;
- at least one uncomplexed biologically active phenolic compound or polyphenol;
- uncomplexed astaxanthin;
- uncomplexed zeaxanthin; and
- uncomplexed coenzyme Q10 in the form of ubiquinone, semiquinone, ubiquinol, or a combination thereof.

11. The nutritional supplement composition of claim 1, comprising:
- at least one biologically active complex in which the phytonutrient compound thereof is derived from olives; and
- at least one biologically active complex in which the phytonutrient compound thereof is derived from algae or vegetables.

12. The nutritional supplement composition of claim 1, wherein:
- the at least one biologically active complex in which the phytonutrient compound is derived from olives is selected from the group consisting of non-covalent carbon-60 fullerene-oleocanthal-triglyceride complexes, non-covalent carbon-60 fullerene-oleacein-triglyceride complexes, non-covalent carbon-60 fullerene-oleuropein-triglyceride complexes, non-covalent carbon-60 fullerene-tyrosol-triglyceride complexes, non-covalent carbon-60 fullerene-hydroxytyrosol-triglyceride complexes and combinations thereof; and
- the at least one biologically active complex in which the phytonutrient compound is derived from algae or vegetables is selected from the group consisting of non-covalent carbon-60 fullerene-astaxanthin-triglyceride complexes, non-covalent carbon-60 fullerene-zeaxanthin-triglyceride complexes, and combinations thereof.

13. The nutritional supplement composition of claim 12, further comprising at least one of an uncomplexed coenzyme Q10 or a non-covalent carbon-60 fullerene-coenzyme-Q10-triglyceride complex.

14. The nutritional supplement composition of claim 1, comprising:
- at least one biologically active complex selected from the group consisting of non-covalent carbon-60 fullerene-oleocanthal-triglyceride complexes, non-covalent carbon-60 fullerene-oleacein-triglyceride complexes, non-covalent carbon-60 fullerene-oleuropein-triglyceride complexes, and combinations thereof; and
- at least one of uncomplexed astaxanthin, uncomplexed zeaxanthin, and uncomplexed coenzyme Q10.

15. A nutritional supplement composition that is oil-based, the nutritional supplement composition comprising:
- a carrier oil base containing at least one triglyceride; and
- at least one biologically active complex in the carrier oil base, the at least one biologically active complex comprising:
  - a first portion comprising a carbon-60 fullerene non-covalently associated with a phytonutrient compound; and
  - a second portion comprising a molecule of the at least one triglyceride from the carrier oil base non-covalently associated with the first portion,
- wherein:
  - the carrier oil base is chosen from olive oils, argan oils, medium-chain triglyceride oils, and combinations thereof;
  - the phytonutrient compound is selected from the group consisting of oleocanthal, oleacein, oleuropein, tyrosol, hydroxytyrosol, carvacrol, honokiol, astaxanthin, zeaxanthin, and coenzyme Q10.

16. The nutritional supplement composition of claim 15, wherein the at least one biologically active complex is selected from the group consisting of non-covalent carbon-60 fullerene-oleocanthal-triglyceride complexes, non-covalent carbon-60 fullerene-oleacein-triglyceride complexes, non-covalent carbon-60 fullerene-oleuropein-triglyceride complexes, non-covalent carbon-60 fullerene-hydroxytyrosol-triglyceride complexes, non-covalent carbon-60 fullerene-carvacrol-triglyceride complexes, non-covalent carbon-60 fullerene-honokiol-triglyceride complexes, non-covalent carbon-60 fullerene-astaxanthin-triglyceride complexes, non-covalent carbon-60 fullerene-zeaxanthin-triglyceride complexes, non-covalent carbon-60 fullerene-coenzyme-Q10-triglyceride complexes, and combinations thereof.

17. The nutritional supplement composition of claim 15, comprising:
- at least one biologically active complex in which the phytonutrient compound thereof is derived from olives; and
- at least one biologically active complex in which the phytonutrient compound thereof is derived from algae or vegetables.

18. The nutritional supplement composition of claim 17, wherein:

the at least one biologically active complex in which the phytonutrient compound derived from olives is selected from the group consisting of non-covalent carbon-60 fullerene-oleocanthal-triglyceride complexes, non-covalent carbon-60 fullerene-oleacein-triglyceride complexes, non-covalent carbon-60 fullerene-oleuropein-triglyceride complexes, non-covalent carbon-60 fullerene-tyrosol-triglyceride complexes, non-covalent carbon-60 fullerene-hydroxytyrosol-triglyceride complexes and combinations thereof; and the at least one biologically active complex in which the phytonutrient compound is derived from algae or vegetables is selected from the group consisting of non-covalent carbon-60 fullerene-astaxanthin-triglyceride complexes, non-covalent carbon-60 fullerene-zeaxanthin-triglyceride complexes, and combinations thereof.

19. The nutritional supplement composition of claim 15, further comprising at least one additional ingredient chosen from:

an uncomplexed carbon-60 fullerene;
at least one uncomplexed biologically active phenolic compound or polyphenol;
uncomplexed astaxanthin;
uncomplexed zeaxanthin;
uncomplexed honokiol; or
uncomplexed coenzyme Q10.

20. The nutritional supplement composition of claim 19 comprising, based on the total volume of the nutritional supplement composition:

a carbon-60 fullerene concentration of from 0.1 g/L to 3 g/L, based on a total amount of (a) complexed carbon-60 fullerene from all biologically active complexes in the nutritional supplement composition and (b) any uncomplexed carbon-60 fullerene present in the nutritional supplement composition;

a phenolic concentration of from 100 ppm to 4000 ppm;

an astaxanthin concentration of from 0.1 g/L to 10 g/L; and a coenzyme Q10 concentration of from 0.1 g/L to 3 g/L.

* * * * *